United States Patent
Hur et al.

(10) Patent No.: US 8,012,727 B2
(45) Date of Patent: Sep. 6, 2011

(54) BIOLOGICAL PRODUCTION METHOD OF PHOTOCONDUCTIVE ARSENIC-SULFIDE (AS-S) NANOTUBE AND STRAIN USED FOR THE SAME

(75) Inventors: Hor-Gil Hur, Gwangju (KR); Ji-Hoon Lee, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 930 days.

(21) Appl. No.: 12/000,554

(22) Filed: Dec. 13, 2007

(65) Prior Publication Data

US 2009/0155876 A1   Jun. 18, 2009

(51) Int. Cl.
*C12P 3/00* (2006.01)
(52) U.S. Cl. ............... 435/168; 435/252.1; 428/364
(58) Field of Classification Search .......... None
See application file for complete search history.

(56) References Cited

U.S. PATENT DOCUMENTS 7,227,066 B1 * 6/2007 Roscheisen et al. ........... 257/40

OTHER PUBLICATIONS

Lee et al., "Biogenic formation of photoactive arsenic-sulfide nanotubes by *Shewanella* sp. strain HN-41." *PNAS*, v.104:51, pp. 20410-20415 (2007).
Lee et al., "Organic Acid-Dependent Iron Mineral Formation by Newly Isolated Iron-Reducing Bacterium, *Shewanella* sp. HN-41." *Geomicrobiology Journal*, v.24, pp. 31-41 (2007).
Newman et al., "Precipitation of Arsenic Trisulfide by *Desulfotomaculum auripigmentum*." *Applied and Environmental Microbiology*, v.63:5, pp. 2022-2028 (1997).
Ji-Hoon Lee, *Environmental and Biogeochemical Significances of Metals Biotransformation by Shewanella*—Thesis for Ph.D. Degree. Department of Environmental Science and Engineering, Gwangju Institute of Science and Technology (2007).

* cited by examiner

*Primary Examiner* — Irene Marx
(74) *Attorney, Agent, or Firm* — The Nath Law Group; Joshua B. Goldberg; Mihsuhn Koh (57) ABSTRACT

Disclosed is a biological method for preparing arsenic sulfide (As—S) compounds. More particularly, the present invention provides a method for production of nanotubes based on As—S compounds including $As_2S_3$ by reacting thiosulfate $S_2O_3^{2-}$ with arsenate $As^{5+}$ through mediation of *Shewanella* sp. strain.

2 Claims, 9 Drawing Sheets

I-V CHARACTERISTICS

BIOLOGICAL PRODUCTION METHOD OF PHOTOCONDUCTIVE ARSENIC-SULFIDE (AS-S) NANOTUBE AND STRAIN USED FOR THE SAME

FIELD OF THE INVENTION

The present invention relates to biological production of arsenic-sulfide (As—S) compound based nanotubes and strains used for the same, more particularly, to a method for biological production of photoconductive As—S compound based nanotubes with improvements over conventionally known physical or chemical production methods, for example, convenience of production and potential use of nanotubes as optoelectronic materials, as well as specific strain used for the same.

DESCRIPTION OF THE RELATED ART

There have been studies and investigations for arsenic sulfide ($As_2S_3$) based nanowires among metal chalcogenides fabricated by chemical methods, and/or tungsten compound ($WS_2$) or molybdenum compound ($MoS_2$) based nanotubes fabricated by chemical methods.

However, such methods usually implemented by chemical procedures have drawbacks such as high production cost and complicated production processes. In addition, there is a requirement for further effort in purification step due to a great amount of impurities generated during production of nano materials.

In order to solve problems generally caused by chemical processes, there has been much ongoing research and development into a plurality of biological methods as alternative proposals. These mostly include environment-friendly production methods using microorganisms and have undesirable problems in that they require a long period of time to isolate desired microorganisms, usually have a small yield of desired products, and often need specific conditions for growth and culture of microorganisms.

Methods for production of As—S compounds using microorganisms are still not disclosed in the related arts. Moreover, it is now very difficult to produce nanotubes useful for manufacturing optoelectronic devices.

SUMMARY OF THE INVENTION

Accordingly, the present invention is directed to solve problems of conventional methods as described above and, an object of the present invention is to provide a method for production of nanotubes based on arsenic sulfide (As—S) compounds (hereinafter often referred to as "As—S based nanotubes") usable as optoelectronic materials, which has improved convenience of production over conventionally known physical and/or chemical processes.

Another object of the present invention is to provide specific strain useful for production of As—S compound based nanotubes which are usable as optoelectronic materials.

A still further object of the present invention is to provide optoelectronic devices containing As—S compound based nanotubes produced according to the method of the present invention described above.

In order to achieve the objects described above, the present invention provides a method for production of nanotubes based on As—S compounds including $As_2S_3$ by reacting thiosulfate $S_2O_3^{2-}$ with arsenate $As^{5+}$ through mediation of Shewanella sp. strain.

Such As—S compound based nanotubes of the present invention have photoconductivity.

The present invention also provides Shewanella sp. strain useful for production of nanotubes based on As—S compounds including $As_2S_3$ by reaction of sodium thiosulfate with sodium arsenate.

Such Shewanella sp. strain according to the present invention is designated to Shewanella sp. strain HN-41 (KCTC 10837BP).

Further, the present invention provides optoelectronic devices containing As—S compound based nanotubes produced by the present invention.

Consequently, the present invention can achieve a biological production method of photoconductive As—S based nanotubes with several advantages in that this method has improved convenience of production over conventionally known physical or chemical processes, economic benefit in view of production cost, and high potential utility of As—S based nanotubes as optoelectronic materials with nanometer size.

BRIEF DESCRIPTION OF THE DRAWINGS

These and other objects, features, aspects, and advantages of the present invention will be more fully described in the following detailed description of preferred embodiments and examples, taken in conjunction with the accompanying drawings. In the drawings.

DETAILED DESCRIPTION OF THE INVENTION

Hereinafter, the present invention will be described in detail.

Microorganisms used in the present invention are substantially *Shewanella* sp. strains, which induce reductive reaction of thiosulfate ($S_2O_3^{2-}$) and arsenate (arsenic oxide) ($As^{5+}$) into sulfide ions ($S^{2-}$) and arsenite ions ($As^{3-}$), respectively, to produce nanotubes based on As—S compounds including $As_2S_3$ with yellow color and photoconductivity.

Such strains were isolated by the following procedure:

First of all, a sample (anaerobic soil or deposits) was placed in a serum bottle containing an anaerobic HEPES-buffered defined medium, which comprises lactate and ferric citrate or lactate and arsenate ($As^{5+}$) available in the field. After carrying this serum bottle to a laboratory, the sample in the bottle was cultured in an incubator at 27 to 30° C. for 3 to 5 days and moved to a new incubator. These steps were repeated seven (7) to nine (9) times. Such cultured strain was spreading on a solid HEPES-buffered defined medium containing agar to collect a single bacteria colony. It was found that the collected single bacterial colony was grown while deriving reductive reaction of ferric citrate or arsenate ($As^{5+}$). Such bacteria were subjected to isolation and identification in the form of single strain.

Genes were extracted from the bacteria isolated according to the above processes and the genes underwent a polymerase chain reaction PCR to amplify 16S rRNA. After sequence analysis of such amplified 16S rRNA, the genes were compared with genes of existing strains available in GenBank for similarity between them.

The strain used in the present invention is generally gram-negative bacteria belonging to anaerobic strains, and has a short rod form. It was known that this strain can use oxygen as an electron acceptor under aerobic environments and utilize a variety of electron acceptors such as iron, manganese, fumarate, thiosulfate and so on under anaerobic environments.

Based on the characteristics described above, the present inventors identified the strain isolated according to the present invention as *Shewanella* sp. strain being one of metal salts reducing bacteria, and thus designated the strain as *Shewanella* sp. strain HN-41, which was deposited with BRC KCTC (Biological Resource Center, Korean Collection for Type Cultures, 52 Eoeun-dong, Yuseong-gu, Daejon 305-333, Republic of Korea) on Aug. 22, 2005 with accession No. KCTC 10837 BP.

The following description demonstrates that the inventive strain can produce As—S compound based nanotubes by reducing thiosulfate ($S_2O_3^{2-}$) and arsenate ($As^{5+}$) into sulfide ions ($S^{2-}$) and arsenite ($As^{3-}$), respectively.

According to the present invention, it was observed that *Shewanella* sp. strain HN-41 did not cause reduction of As(V) when the strain was added to a medium as the only electron acceptor. And, a little growth of the strain was observed by adding $S_2O_3^{2-}$ as the only electron acceptor to the medium. Furthermore, in a water-soluble solution phase, there was very little production of $S^{2-}$ which was substantially impossible to measure.

Figure 1:
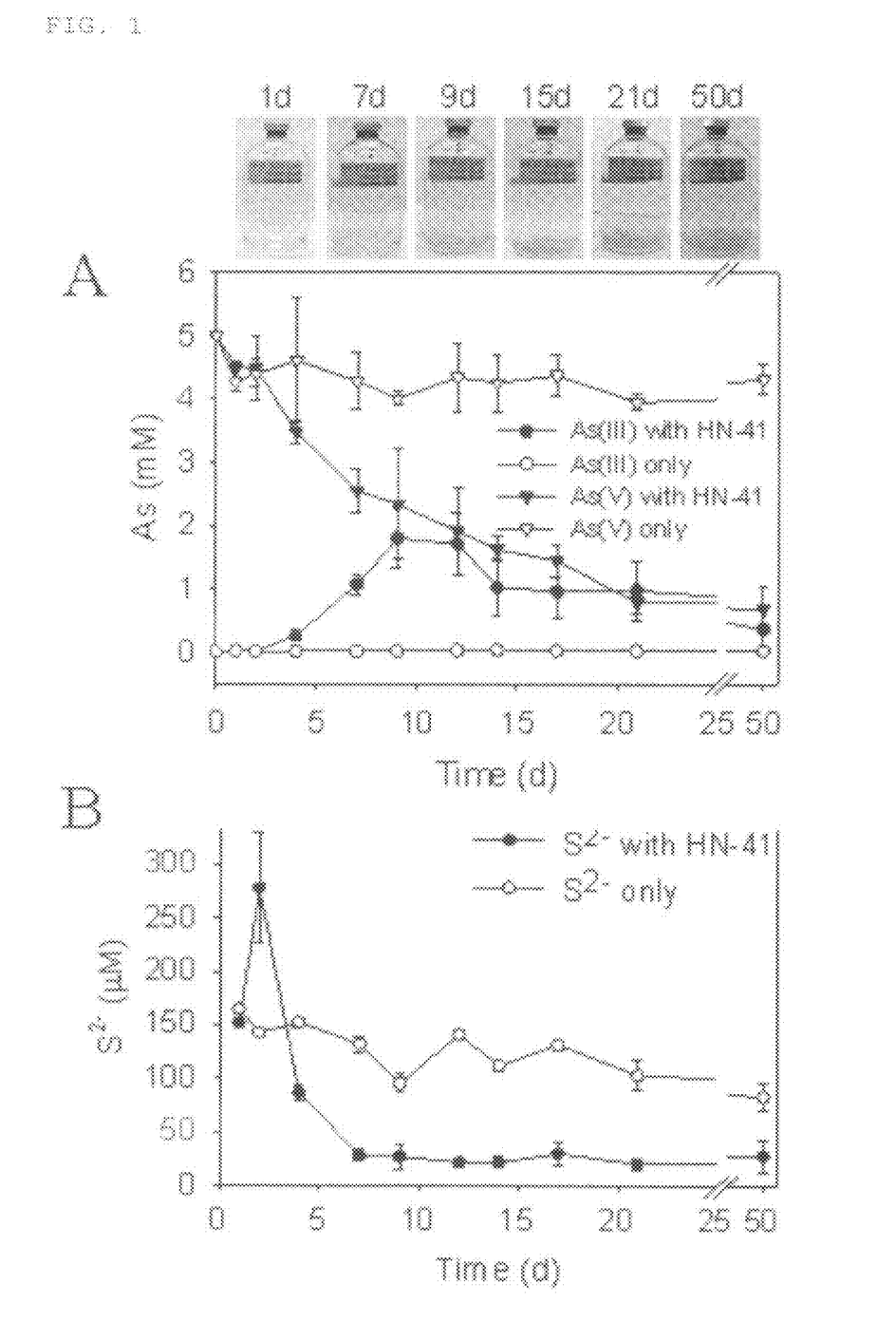
FIG. 1 shows concentrations of arsenic (A) and sulfide ions in a water-soluble solution phase (B), which were generated by reductive reaction of thiosulfate, versus time when Shewanella sp. strain HN-41 is cultured for production of As—S based nanotubes.

As shown in FIGS. 1A and 1B, neither of As(III) nor $S^{2-}$ was produced and no reduction of As(V) into As(III) was observed in a non-inoculation medium containing As(V) and $S_2O_3^{2-}$ as a control group. When a supernatant comprising a non-inoculation medium which contains As(V) and $S^{2-}$ or As(III) and $S^{2-}$, or an extra-cellular fluid type polymeric material derived from HN-41 strain after extinction of the strain using antibiotics was added to As(V) and $S^{2-}$ or As(III) and $S^{2-}$, no precipitate with yellow color was generated in the solution. In case that HN-41 was cultured in a HEPES buffer medium, the cultured material did not show a strong acidic condition caused by decomposed sulfide leading to chemical reduction of As(V) and this means that reduction of As(V) into As(III) is biologically mediated by HN-41 strain.

Although it is known that bacteria including *Shewanella* sp. strains can reduce As(V) into As(III) by respiration and/or detoxification, a reduction mechanism of As(V) using HN-41 strain according to the present invention is not still clearly disclosed. In order to identify the reduction mechanism, PCR analysis was implemented using a primer set designed for amplification of well conserved arrA genes, which encode enzymes participating in respiratory As(V) reduction. As a result of PCR analysis, it was found that fragments with desirable size are obtained but have less similarity with arrA genes of *Shewanella* sp. strains. The above results are expected because *Shewanella* sp. strain HN-41 according to the present invention includes arrA genes which are much different from those discovered in general bacteria, otherwise, the strain uses alternative reduction mechanism.

However, arsB and arsC genes encoding arsenite outflow pump and arsenite reduction enzyme, respectively, were detected from HN-41 strain by PCR analysis and this fact suggests that HN-41 strain reduces arsenate for detoxification rather than respiration. HN-41 arsB and arsC genes exhibit protein similarities of 77.0 and 76.4%, respectively, compared with arsB and arsC genes (AY271310) of *Shewanella* sp. strain ANA-3.

From the above facts, it is considered that enzymatic reduction of As(V) into As(III) by arsC product and, in turn, reduction of $S_2O_3^{2-}$ into $S^{2-}$, both of which are practiced in a medium containing As(V) and $S_2O_3^{2-}$, have reference to growth of *Shewanella* sp. strain HN-41 according to the present invention.

A process for production of As—S compound based nanotubes using *Shewanella* sp. strain HN-41 according to the present invention will be more particularly described as follows.

*Shewanella* sp. strain HN-41 of the present invention is cultured in a solid LB medium at 25 to 35° C. under aerobic conditions and the cultured strain may be used as an inoculation strain. The inoculation strain is introduced to an anaerobic serum bottle medium containing a reaction substrate and cultured at 30° C., thereby yielding the purposed As—S compound based nanotubes.

A starting material or substrate available in preparation of $As_2S_3$ using *Shewanella* sp. strain HN-41 comprises a variety of thiosulfates and arsenic oxides, that is, arsenates. Illustrative examples of the starting substrate include sodium salts of thiosulfuric acid and arsenic acid. Such sodium salts are added to a desired medium and followed by addition of an incubation solution containing *Shewanella* sp. strain HN-41 described above according to the present invention to produce $As_2S_3$.

In addition to $As_2S_3$, other compounds such as AsS, $As_4S_3$, $As_4S$ and the like are also obtainable by the above procedures. Such As—S compounds have substantially same properties with organic fiber materials in form of a longitudinal cylinder.

As a result of observation, it was found that a longitudinal cross-sectional face of the compound is in a tube form.

Furthermore, $As_2S_3$ obtained according to the present invention has photoconductivity, which was identified by intrinsic properties of semiconductor demonstrated on a current-voltage curve when $As_2S_3$ was exposed to visible light. Because of photoconductivity, $As_2S_3$ can be preferably utilized as optoelectronic materials with nanometer size.

Consequently, As—S compound based nanotubes produced by the present invention can be applied in manufacturing sensor, waveguide, photonic crystal, photolithography, etc.

Hereinafter, the present invention will be more particularly described by the preferred examples. However, these are intended to illustrate the invention as preferred embodiments of the present invention and do not limit the scope of the present invention.

EXAMPLE 1

Culture of Inoculation Strain

After culturing *Shewanella* sp. strain HN-41 in a solid LB (Luria-Bertani) medium at 30° C. under aerobic conditions for 24 hours, bacteria were collected using a loop, centrifuged and washed well using an incubating solution separately prepared, for example, a HEPES-buffered defined medium. The washed strain was again suspended in the incubating solution to prepare a strain containing solution with optical density OD of about 2.0 at 600 nm.

EXAMPLE 2

Culture of Strain for Production of $As_2S_3$

Anaerobic HEPES-Buffered Defined Medium
The following compounds were dissolved in 1 L of the medium.

| | |
|---|---|
| $NaHCO_3$ | 2.5 g |
| $CaCl_2$ | 0.06 g |
| β-glycerophosphoric acid disodium salt | 0.06 g |
| $NH_4Cl$ | 1 g |
| $MgCl_2 \cdot 6H_2O$ | 0.2 g |
| KCl | 0.1 g |
| NaCl | 10.0 g |
| HEPES (N-2-hydroxyethylpiperazine-N'-2-ethane sulfonic acid) | 7.2 g |
| Yeast extract | 0.1 g |
| Resazurin (0.05%) | 0.1 mL |
| Trace element containing solution[1] | 10 mL |
| Vitamin containing solution[2] | 1 mL |

[1]Trace elements containing solution (1 liter of final volume)
[2]Vitamin containing solution (1 liter of final volume)

The above ingredients were dissolved in 1 L of distilled water to prepare an incubating solution, and nitrogen gas (100%) was injected into the solution and boiled during agitation. After boiling the incubating solution till blue color of resazurin completely disappeared, nitrogen gas was injected into the treated solution while cooling the solution. pH value of the cooled solution was adjusted to pH 7.5 using 10N NaOH. The resultant incubating solution was divided and placed in several serum bottles and nitrogen gas was injected into each of the serum bottles. The serum bottles were plugged by butyl rubber stoppers and tightly sealed by aluminum stoppers. The prepared serum bottles containing the incubating solution were subjected to sterilization using an autoclave.

The above trace element containing solution and the vitamin containing solution include the following ingredients, respectively.

| | |
|---|---|
| Nitriloacetic acid | 1.5 g |
| $FeCl_2 \cdot 4H_2O$ | 0.2 g |
| $MgCl_2 \cdot 6H_2O$ | 0.1 g |
| $Na_2WO_4 \cdot 2H_2O$ | 0.02 g |
| $MnCl_2 \cdot 4H_2O$ | 0.1 g |
| $CoCl_2 \cdot 6H_2O$ | 0.1 g |
| $CaCl_2 \cdot 2H_2O$ | 1.0 g |
| $ZnCl_2$ | 0.05 g |
| $CuCl_2 \cdot 2H_2O$ | 0.002 g |
| $H_3BO_3$ | 0.005 g |
| $Na_2MoO_2 \cdot 2H_2O$ | 0.01 g |
| NaCl | 1 g |
| $Na_2SeO_3$ | 0.017 g |
| $NiCl_2 \cdot 6H_2O$ | 0.024 g |
| Biotin | 20 mg |
| Folic acid | 20 mg |
| Pyridoxine HCl ($B_6$) | 100 mg |
| Thiamin HCl ($B_1$) | 50 mg |
| Riboflavin ($B_2$) | 50 mg |
| Nicotinic acid | 50 mg |
| Pantothenic acid | 50 mg |
| Cyanobalamin crystalline ($B_{12}$) | 1 mg |
| p-aminobenzoic acid | 50 mg |
| lipoic acid | 50 mg |

Strain Culture
To the above prepared anaerobic serum bottle medium, 20 to 50 mM lactate such as sodium DL-lactate, 10 mM sodium thiosulfate $Na_2S_2O_3.5H_2O$ and 5 mM sodium arsenate $Na_2HAsO_4.7H_2O$ were added, followed by injection of the prepared strain solution ($OD_{600}=2$) into the medium mixture by a syringe to produce a final incubating solution containing 1% by volume of the strain solution. The final incubating solution was cultured at 30° C.

EXAMPLE 3

Production of As—S Based Nanotubes and Characterization Thereof

As shown in FIG. 1, $As^{5+}$ was reduced into $As^{3+}$ to result in decrease of $As^{5+}$ concentration during progress of the culture. On the contrary, $As^{3+}$ concentration was apt to be initially increased, then, decreased again and this indirectly demonstrated that $As^{3+}$ was precipitated in the form of As—S compound to cause reduce concentration of $As^{3+}$ in a water-soluble solution phase of the incubating solution. Similarly, thiosulfate ($S_2O_3^{2-}$) was reduced into sulfide ions ($S^{2-}$) to cause initial increase and following decrease of $S^{2-}$ concentration in the water-soluble solution phase of the incubating solution. This means that $S^{2-}$ was evaporated into an upper space in the bottle to be cultured or was precipitated in the form of As—S compound, thereby reducing the concentration of $S^{2-}$ in the water-soluble solution phase. From photographs of the bottles to be cultured depending on time as shown in FIG. 1, yellow As—S compound precipitate came into existence at 9 days after culture.

Figure 2:
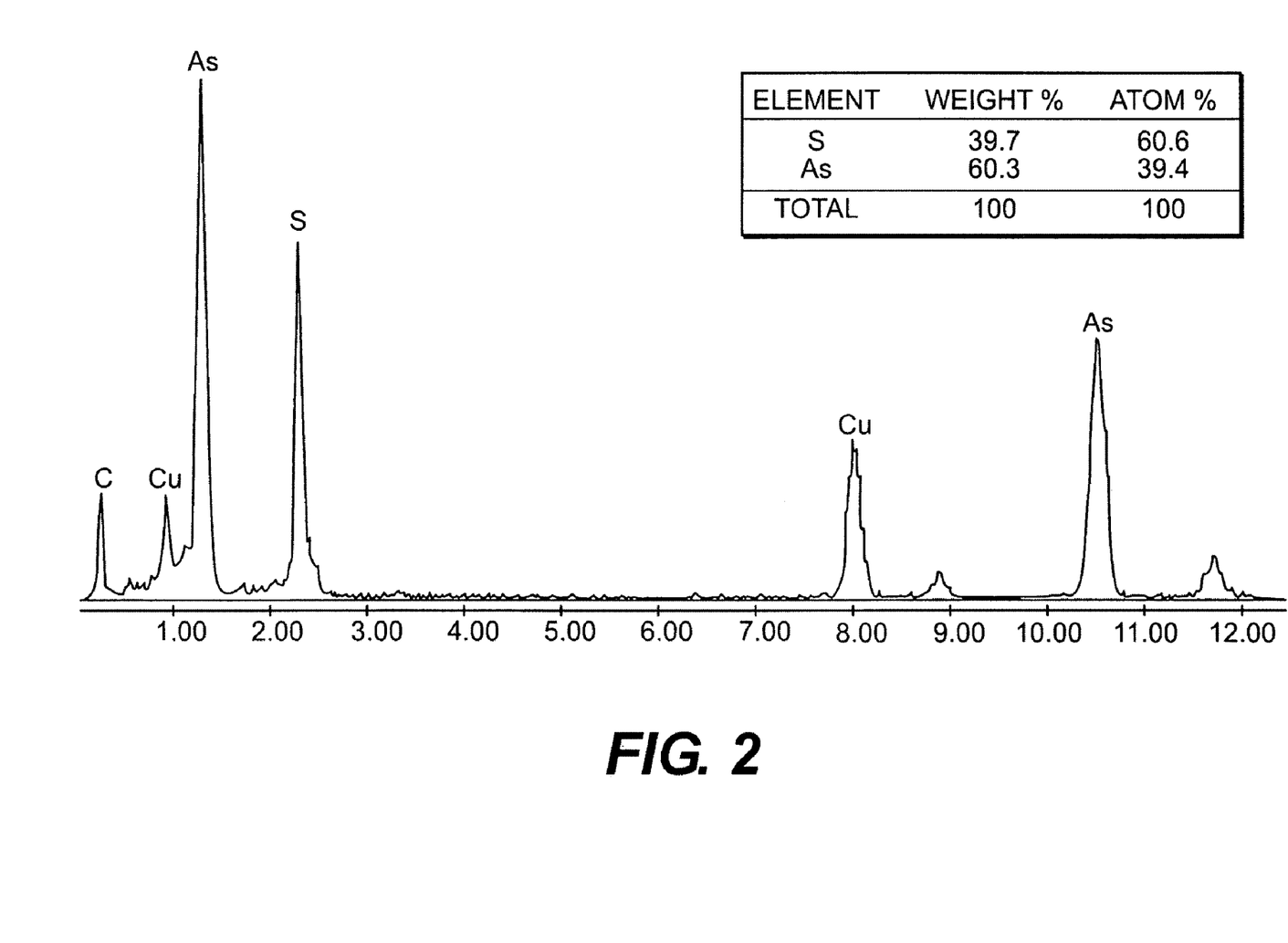
FIG. 2 illustrates results of an energy dispersion X-ray spectroscopic (EDX) experiment for single As—S based nanotubes produced using Shewanella sp. strain HN-41.

In order to determine composition of the As—S compound, a single As—S compound was analyzed using EDX spectroscopy instead of aggregates of the As—S compounds. As a result of the analysis, it was found that As—S compound initially generated (at 9 days) has composition of $As_2S_3$ (see FIG. 2).

Figure 3:
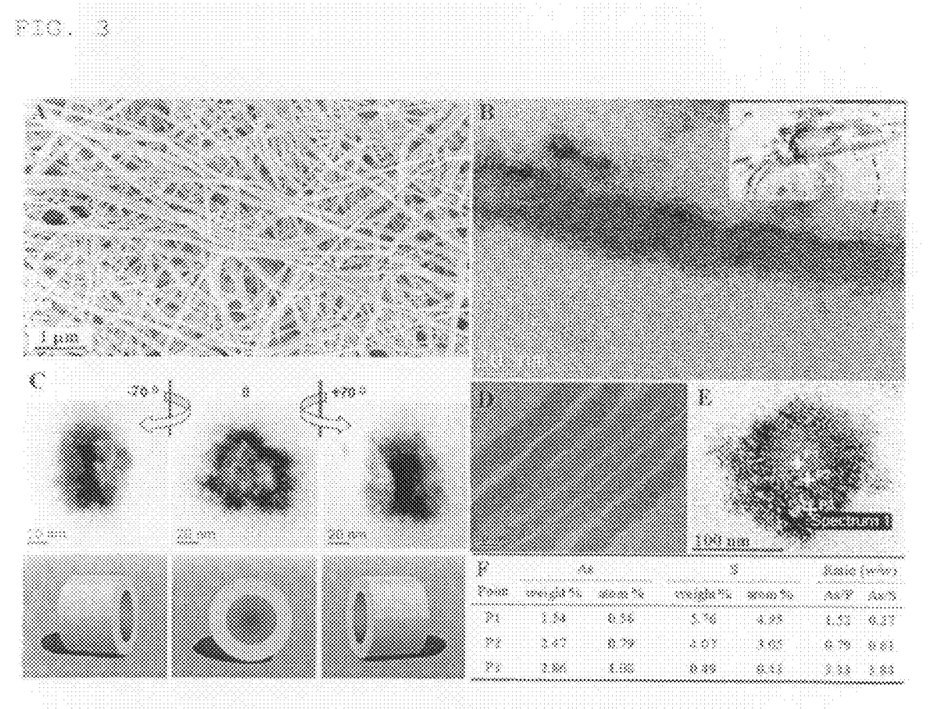
FIG. 3 shows electron microscopic images of As—S based nanotubes, in particular: (A) scanning electron microscopic (SEM) images; (B) longitudinal transmission electron microscopic (TEM) images with bar size of 20 nm; (C) transverse TEM three-dimensional computed tomographic images; (D) overall TEM images; and (E) and (F) scanning transmission electron microscopic (STEM)-EDX images of transverse cross-sectional face of As—S based nanotubes.

Analysis of a biologically originated As—S compound by means of electron microscopy demonstrated that the compound exhibited an appearance like an organic fibrous material in form of an elongated cylinder (see FIG. 3). Longitudinal cross-sectional face of the compound in the form of the elongated cylinder was observed using TEM. As a result, it was found that the compound has a tube like form (see FIG. 3B). From a result of three-dimensional CT, the compound was represented to obviously have a nanotube form (see FIG. 3C). Additionally, it was identified from EDX analysis for transverse cross-sectional face of As—S based nanotubes that arsenic content was increased from inner side to outer side of the cross-sectional face (see FIGS. 3E, 3F and 4).

Figure 5:
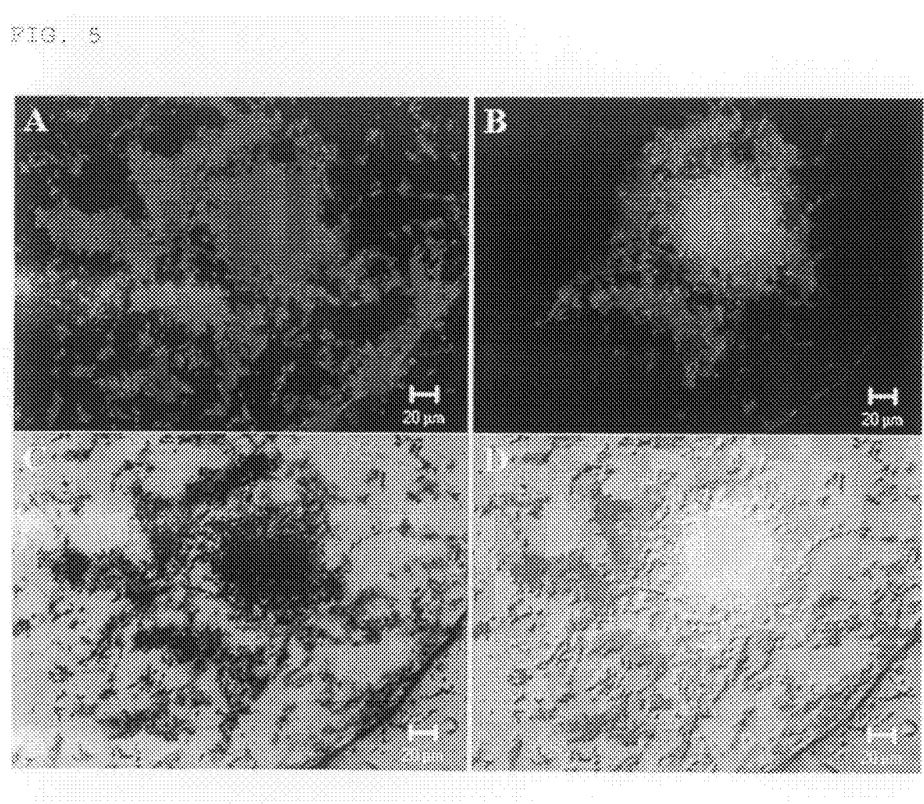
FIG. 5 illustrates results obtained by confocal laser scanning microscope (CLSM) observation of $As_2S_3$, in particular; (A) exopolysaccharides stained by fluorescent dyes such as lectin PHA-L; (B) bacteria stained by SYT09; and (C) optical images and (D) fluorescence images of $As_2S_3$ interposed between exopolysaccharides.

It is expected that external shape of As—S based nanotubes is formed by extra-cellular polymeric substance (EPS) or exopolysaccharides to fabricate a framework, which is formed by outer cell wall by bacteria. This fact was proved from a result of CLSM analysis for As—S compound interposed between EPSs and/or exopolysaccharides (see FIG. 5).

Figure 4:
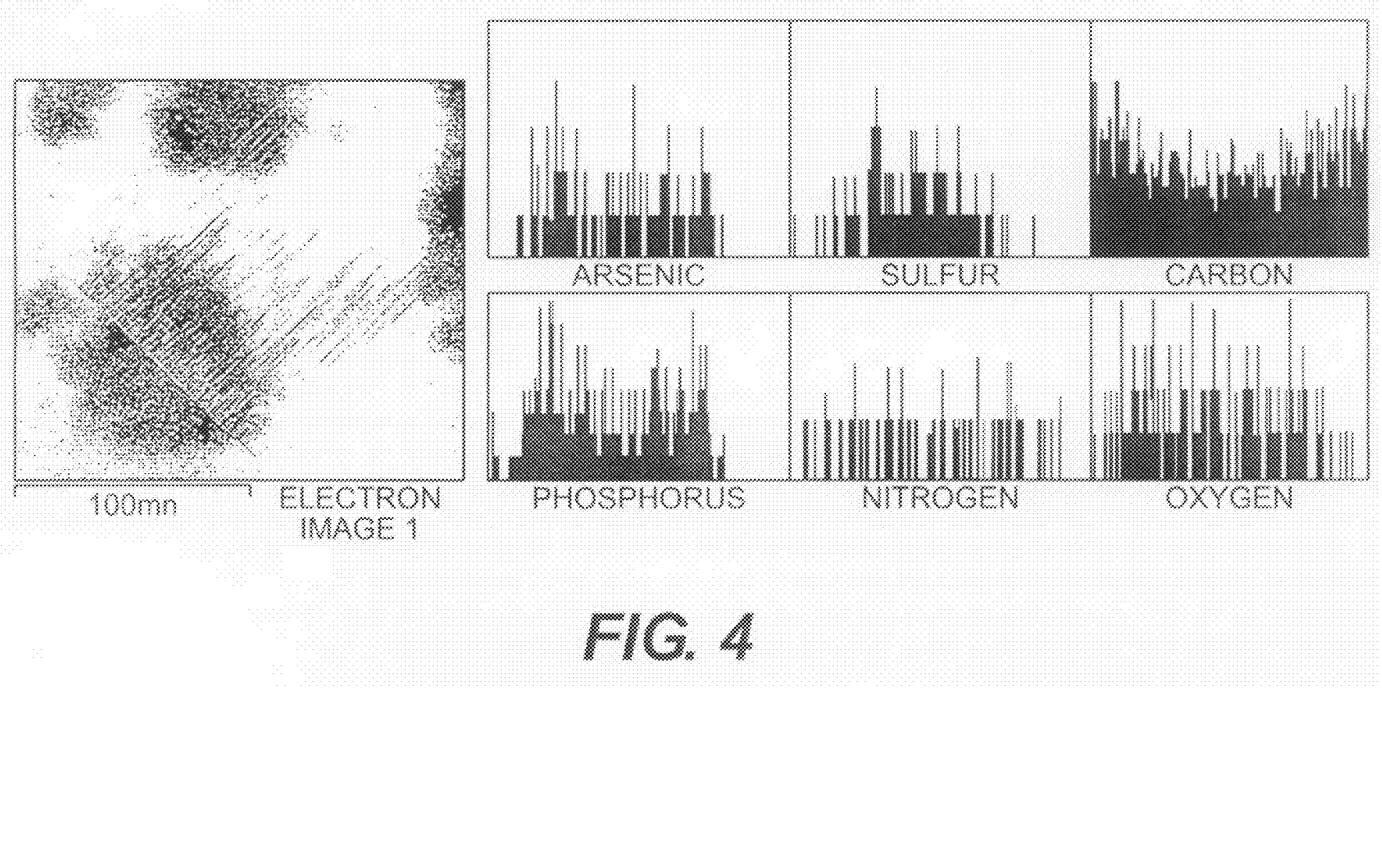
FIG. 4 illustrates results obtained by STEM-EDX linear scanning observation of As—S based nanotubes.
Figure 6:
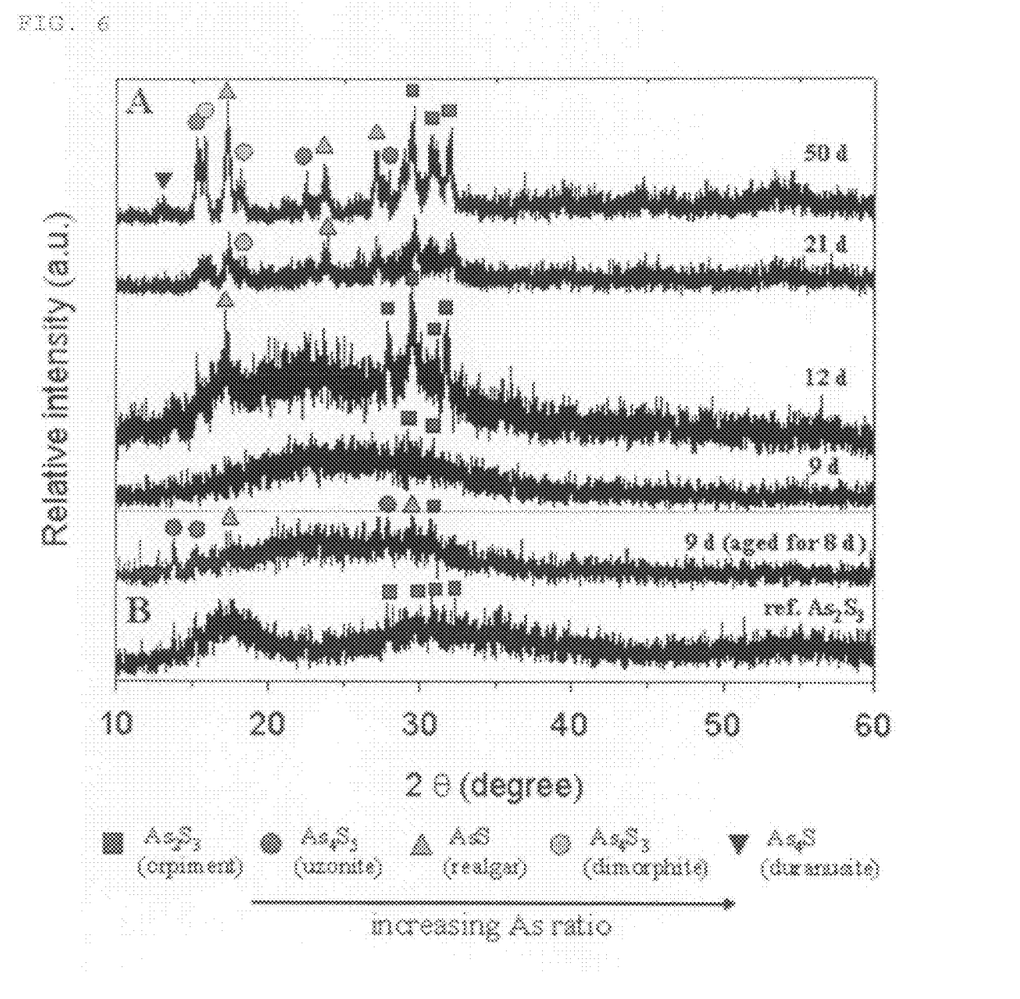
FIG. 6 illustrates results obtained by X-ray diffraction analysis of As—S based nanotubes, in particular: (A) patterns of a sample at respective existing points; (B) a pattern of a sample at 9 days which was obtained after exposing the sample for 8 days to visible light; and, at the lowest position, a pattern of a reference $As_2S_3$ available in the market.
Figure 7:
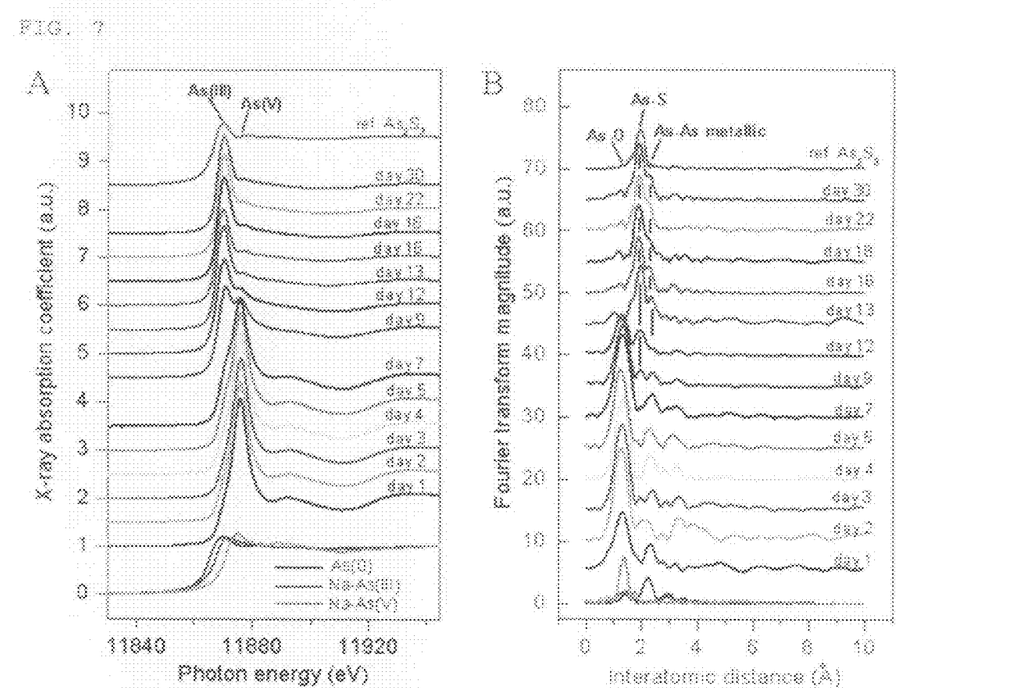
FIG. 7 illustrates results of structural analysis for As—S based nanotubes, which were biologically produced, versus time by X-ray absorption spectroscopy, in particular: (A) XANES spectrum; and (B) EXAFS spectrum after Fourier transform.

XRD analysis depending on the culturing time demonstrated that As—S compounds with increased As content such as AsS, $As_4S_3$ and $As_4S$, were generated from initial and substantially pure $As_2S_3$ (see FIG. 6). This result is correlated with increase of As content from inner side to outer side of the transverse cross-sectional face as illustrated in FIGS. 3E, 3F and 4. Such correlation was proved by X-ray absorption spectroscopy from the facts that initial $As^{5+}$ was reduced into $As^{3+}$ during progress of the culture and metal bonds such as $As^0$—$As^0$ bonds in form of elements were monitored over time (see FIG. 7). These results can be interpreted to correspond to increase of As content rate from inner side to outer side of the transverse cross-sectional face of As—S based nanotubes (see FIGS. 3E, 3F and 4) and interposition of As—S compound with increased As content between EPSs and/or exopolysaccharides versus time as determined by XRD analysis. Briefly, there are generated pure $As_2S_3$ at a point of initial production of As—S based nanotubes and the pure $As_2S_3$ is more reduced into $As^O$ in form of elements on external surface of the nanotubes with the lapse of time and, therefore, to produce As—S compound having high As content.

EXAMPLE 4

Photoconductivity of As—S Based Nanotubes

Figure 8:
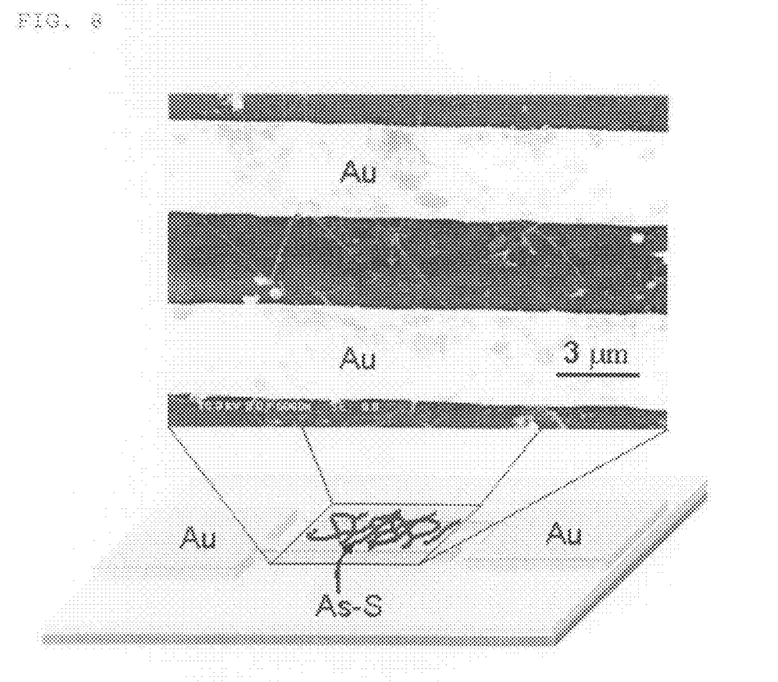
FIG. 8 illustrates a diagram and a SEM image of As—S based nanotubes used to join two gold electrodes with micrometer size.
Figure 9A:
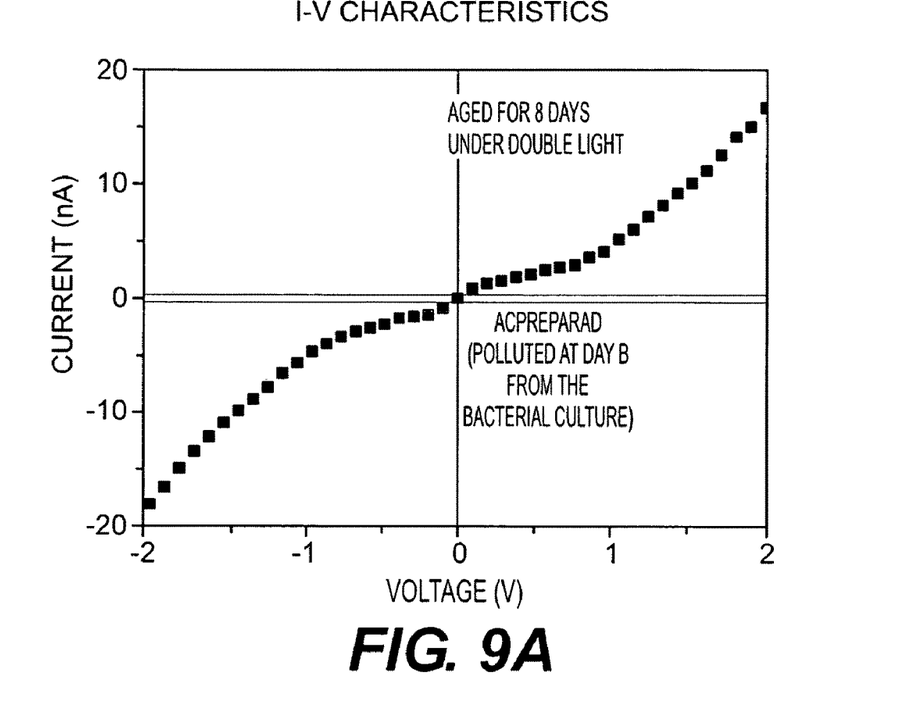
FIG. 9 illustrates electrical and/or optoelectronic characteristics of As—S based nanotubes produced using *Shewanella* sp. strain HN-41, in particular: (A) effects of air exposure and (B) temperature to I-V (current-voltage) characteristics of As—S based nanotubes; (C) optoelectronic properties of photo-luminescence spectrum at 25° C.; and (D) results of photo-current measurement by exposure of a $As_2S_3$ sample at 9 days to UV.
Figure 9B:
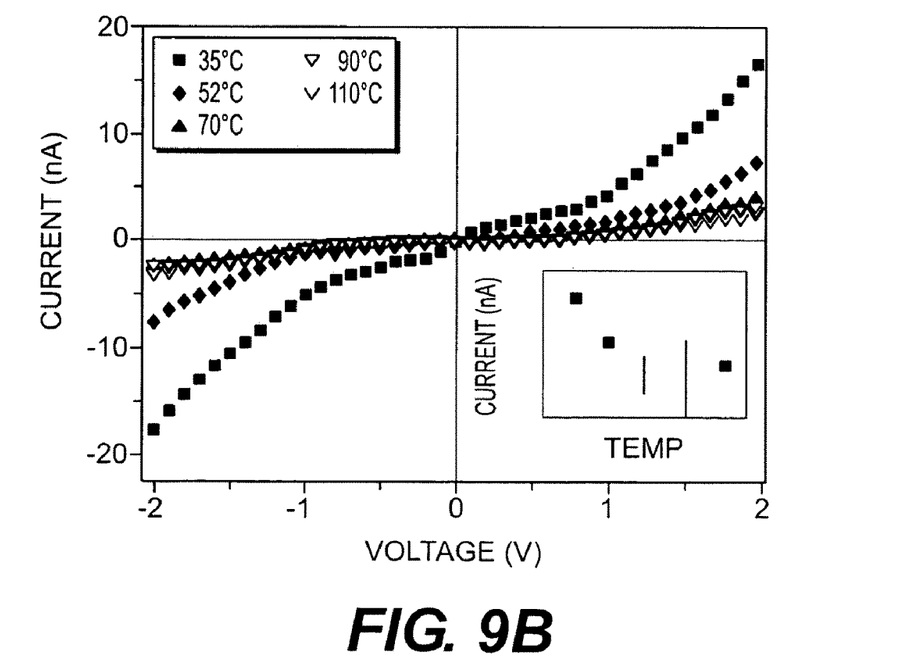

As shown in a diagram of FIG. 8, As—S based nanotubes obtained according to the examples were placed on gold electrodes with micrometer size to join the electrodes together and an electrical experiment was performed on the linked electrodes. From current-voltage (I-V) curves (see FIGS. 9A and 9B), no reaction was observed in case of the experiment using a sample at 9 days after the culture without any pre-treatment while there was I-V correlative reaction with semiconductor like properties if a sample underwent the experiment after exposing the sample to visible light for 8 days (see FIG. 9A). From I-V correlative reaction of the exposed sample depending on temperature in the latter case, the sample exhibited decrease of the correlative reaction, which is one of typical properties of metal, as the temperature was increased (see FIG. 9B).

Figure 9C:
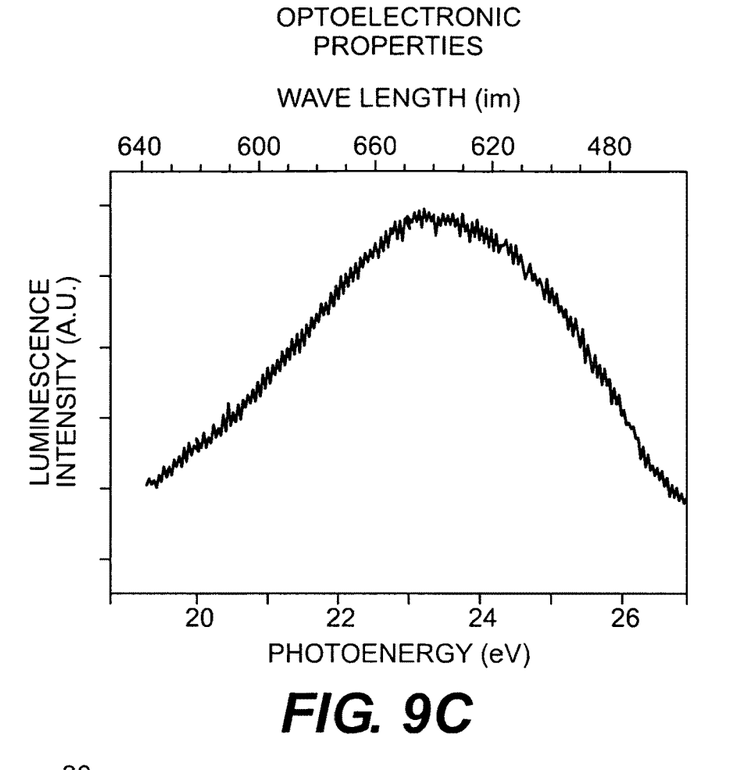
Figure 9D:
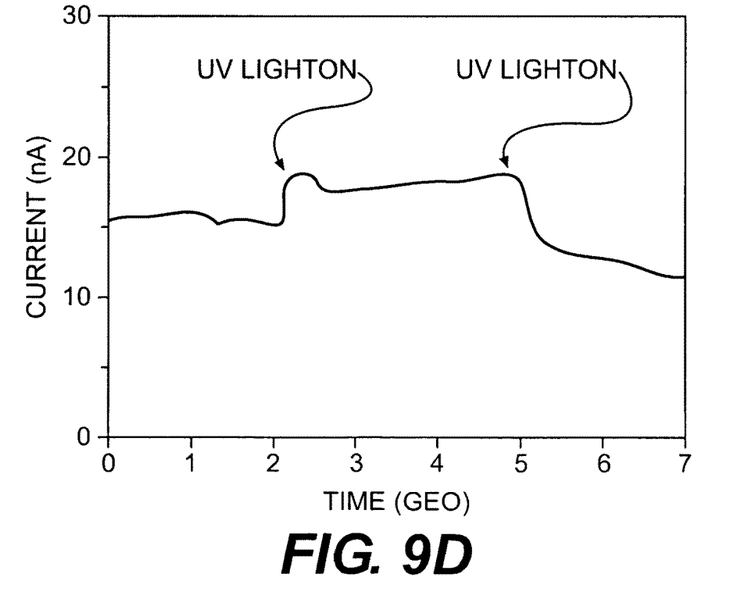

From photo-luminescence spectrum monitored in order to determine optical properties of As—S based nanotubes, there was a luminescence peak of 2.34 eV at 530 nm substantially overlapped with a photonic band gap of 2.4 eV for reference $As_2S_3$ bulk materials (see FIG. 9C). For measurement of photo-current during UV exposure in order to determine photosensitivity of As—S based nanotubes, the photo-current was increased to 18 nA during UV exposure compared to 16 nA without the UV exposure, while the photo-current was decreased to a base level if UV radiation was stopped (see FIG. 9D). Theses results demonstrated that the biologically originated As—S compound based nanotubes according to the present invention have photosensitivity.

While the present invention has been described with reference to the preferred examples, it will be understood by those skilled in the art that various modifications and variations may be made therein without departing from the scope of the present invention as defined by the appended claims.

What is claimed is:

1. A method of preparing nanotubes comprising reacting thiosulfate $S_2O_3^{2-}$ with arsenate $As^{5+}$ through contacting with *Shewanella* sp. strain HN-41 (KCTC 10837BP).

2. The method according to claim 1, wherein the nanotubes have photoconductivity.

* * * * *